US005436139A

United States Patent [19]

Rutter et al.

[11] Patent Number: 5,436,139

[45] Date of Patent: Jul. 25, 1995

[54] NON-PASSAGEABLE VIRUS

[75] Inventors: William J. Rutter; Howard M. Goodman, both of San Francisco, Calif.

[73] Assignee: The Regents of the University of California, Alameda, Calif.

[21] Appl. No.: 89,993

[22] Filed: Jul. 8, 1993

Related U.S. Application Data

[63] Continuation of Ser. No. 571,331, Aug. 22, 1990, abandoned, which is a continuation of Ser. No. 513,055, Jul. 12, 1983, abandoned, which is a continuation of Ser. No. 107,267, Dec. 21, 1979, abandoned, which is a continuation-in-part of Ser. No. 41,909, May 24, 1979, abandoned.

[51] Int. Cl.$^6$ .............................................. C12P 21/06

[52] U.S. Cl. .................................. 435/693; 435/71.1; 435/172.3; 435/252.33; 435/320.1; 536/23.72; 536/24.1; 530/350

[58] Field of Search .................... 435/69.1, 69.3, 70.1, 435/71.1, 91, 172.3, 252.33, 320.1; 536/23.1, 23.72, 24.1; 514/2, 44; 530/350, 826; 935/9, 12, 39, 44, 47

[56] References Cited

U.S. PATENT DOCUMENTS

| | | | |
|---|---|---|---|
| 4,428,941 | 1/1984 | Galibert et al. | 424/177 |
| 5,196,194 | 3/1993 | Rutter et al. | 424/89 |

OTHER PUBLICATIONS

Valenzuela et al., Nature, vol. 280, No. 5725, 30 Aug. 1979, pp. 815–819.

Galibert et al, Nature, vol. 281, 25 Oct. 1979, pp. 646–650.

Burrell et al, Nature, vol. 279, 3 May 1979, pp. 43–47.

*Primary Examiner*—Christine M. Nucker
*Assistant Examiner*—Laurie Scheiner
*Attorney, Agent, or Firm*—Morrison & Foerster

[57] ABSTRACT

The present invention is directed to an expression vector containing DNA which encodes recombinant full-length hepatitis B surface antigen protein wherein said vector is free of DNA encoding hepatitis B core antigen protein in a microorganism.

12 Claims, 6 Drawing Sheets pEco63 DNA (pBR325/DANE)

NON-PASSAGEABLE VIRUS

This application is a continuation of U.S. Ser. No. 07/571,331 filed 22 Aug. 1990, and now abandoned which is a continuation of U.S. Ser. No. 06/513,055 filed 12 Jul. 1983 and now abandoned, which is a continuation of U.S. Ser. No. 06/107,267 filed 21 Dec. 1979 and now abandoned, which is a continuation-in-part of U.S. Ser. No. 06/041,909 filed 24 May 1979 now abandoned. This application is also related to two applications filed as divisionals of U.S. Ser. No. 07/513,055 which have now issued as U.S. patents; U.S. Ser. No. 06/127,228 filed 1 Dec. 1987 which issued as U.S. Pat. No. 4,935,235 and U.S. Ser. No. 06/679,621 filed 1 Dec. 1984 which has now issued as U.S. Pat. No. 5,196,194.

BACKGROUND AND PRIOR ART

The present invention relates to the study of virus-caused diseases. In particular, the invention relates to viruses that with current technology fail to multiply in cultured cells or embryonic tissues, and hence cannot be produced in quantity. Sometimes they do not produce recognizable cytopathology. Therefore their biological effects have been difficult to study. For the most part, such viruses can only be obtained from humans accidentally or voluntarily infected or from infected higher primates, only occasionally can they be obtained from infected lower species. Such viruses are termed herein non-passageable viruses, or NP-viruses, in recognition of the fact they either cannot be maintained or replicated by passage through tissue culture cells, embryonic tissues, or lower organisms or that it is difficult or impractical to do so. The diseases caused by such viruses may have long latent periods, and sometimes result in derangement of the patient's immune system or in carcinogenic transformation. Examples of such viruses include the Hepatitis B Virus (HBV), the "slow" viruses such as the causative agent of kuru, and the viral agent implicated in the etiology of multiple sclerosis, and the xenotropic viruses, such as the C-type particles implicated in the causation of certain tumors. NP viruses may be associated with chronic crippling or wasting diseases, or with cancer. In one case, HBV, there is evidence for dual pathogenicity, in as much as there is strong evidence linking this virus to primary carcinoma of the liver as well as to hepatitis.

In view of the serious and insidious health hazard presented by NP viruses, there is a need of a biological system of general utility to enable research on these viruses to go forward. provide means for the production of genetically pure viral antigens and antibodies thereto and permit production of viral components in desired amounts. The present invention provides such a biological system of general utility for enabling a vast amount of research which is currently impossible due to the nature of NP viruses. The system is also useful for the study of passageable viruses, offering the advantages of reduced biohazard, the capability to synthesize and modify specific virus-coded proteins, and to obtain quantities of viral DNA and virus-coded proteins sufficient for chemical and biochemical analysis, and for the production of vaccines. The nature of the system and the practice of the invention have been demonstrated with HBV. Further background relating to HBV, and the terminology employed in the art, will be discussed, infra.

Until recently, hepatitis has been a disease characterized primarily in terms of its symptoms and epidemiology. In 1967, Blumberg and co-workers first described an antigen associated with infection by hepatitis type B. (See, Blumberg, B.S., *Science* 197, 17 (1977)). Since then, extensive research has contributed a wealth of information about the disease. The causative agent is a DNA virus known as Hepatitis B Virus (HBV). The serum of infected patients contains a variety of particle types associated with infection. The whole virus particle is believed to be essentially spherical and 42 nm in diameter, comprising an envelope, a core and DNA, and termed the "Dane" particle, after its discoverer (Dane, D.S. et al., *Lancet,* 1970-I, 695 (1970)). The envelope contains the surface antigen (HBsAg), discovered by Blumberg. The core contains an immunologically distinct antigen, HBcAg. The DNA isolated from Dane particles is circular and contains varying length single-stranded regions, Summers, J. et al., *Proc. Nat. Acad. Sci. USA* 72, 4597 (1975); Landers, T. A. et al., *J. Virol.* 23, 368 (1977); Fritsch, A. et al., *C. R. Acad. Sci. Paris D* 287,1453 (1978). The surface antigen is found in the serum of persons infected with HBV and in certain carrier states. Antibodies to HBsAg are found in the serum of patients who have been infected with HBV. Antibodies to the core antigen are also found in certain carrier states. A radioimmunoassay has been developed for HBsAg, Ling, C. M. et al., *J. Immunol.* 109, 834 (1972), and for anti-HBsAg, Hollinger, F. et al., *J. Immunol.* 107, 1099 (1971).

The HBsAg is an immunochemically defined material associated with the envelope of the virus. Previous studies indicate that HBsAg comprises several components of varying antigenicity, including both glycosylated and non-glycosylated proteins as major components (Peterson, D. L., et al., *Proc. Nat. Acad. Sci. U.S.A.* 74, 1530 (1977); Peterson, D. L., et al., in *Viral Hepatitis, A Contemporary Assessment of Etiology, Epidemiology, Pathogenesis and Prevention* (G. N. Vyas, S. N. Cohen and R. Schmid, eds.), pp. 569–573, Franklin Institute Press, Philadelphia, 1978). In addition, lipid and several additional protein components have been reported to be present in surface antigen preparations, Shi, J. W. K. and Gerin, J. L., *J. Virol.* 21, 347 (1977). The major protein components were reported as having molecular weights (M.W.) of 22,000 and 28,000 daltons for the non-glycosylated and glycosylated proteins, respectively, based upon sodium dodecyl sulfate (SDS), gel electrophoresis, Peterson, et al. (1977), supra. An N-terminal sequence of 9 amino acids of the 22,000 M.W. protein, isolated from plasma of a human carrier of HBsAg by preparative SDS gel electrophoresis was reported to be Met-Glu-Asn-Ile-Thr-(Ser) or (Cys)-Gly-Phe-Leu (Peterson, et al., 1977, supra.

Standard abbreviations are used herein to denote amino acid sequences:

| | |
|---|---|
| Ala = Alanine | Cys = Cysteine |
| Gly = Glycine | His = Histidine |
| Glu = Glutamic acid | Lys = Lysine |
| Gln = Glutamine | Leu = Leucine |
| Asp = Aspartic acid | Ile = Isoleucine |
| Asn = Asparagine | Val = Valine |
| Arg = Arginine | Ⓜ or Met = Methionine |
| Ser = Serine | Tyr = Tyrosine |
| Thr = Threonine | Phe = Phenylalanine |
| Trp = Tryptophan | Pro = Proline |

All amino acids are in the L-configuration unless stated otherwise. In some instances herein, methionine is designated by Ⓜ to signify its potential role in translation initiation. An N-terminal sequence of 19 amino acids for a protein similarly isolated was reported to be: Met-Glu-Asn-Ile-Thr-Ser-Gly-Phe-Leu-Gly-Pro-Leu-Leu-Val-Ser-Gln-Ala-Gly-Phe. (Peterson, et al., 1978, supra.). The non-glycosylated protein was reportedly immunogenic, but the glycosylated peptide, isolated as described by Peterson et al., 1977, supra, was not. However, other workers have reported a glycosylated peptide component which was immunogenic, Gerin, J. L., et al., in *Viral Hepatitis*, supra, pp. 147-153 (1978). The discrepancy has not been fully explained. It is known that the immunogenicity of the surface antigen proteins is sensitive to conformation changes. Possibly the use of detergents in the isolation and purification of surface antigen proteins from serum or plasma leads to diminished immunological reactivity.

The ability to detect the surface and core antigens has proven of great clinical value, especially for the screening of potential blood donors, since transfusion is one of the more common modes of HBV transmission in developed countries. Presently available sources of Dane particles for partially purified HBsAg limit the quality and quantity of antibody which can be produced. The virus cannot be grown in culture and can only be obtained from infected human patients or after infection of higher primates. Therefore, there is no means for maintaining stocks of HBV or for obtaining desired amounts of the virus or any of its components. The virus exerts no cytopathic affects on cultured cells or tissues, so that no means for measurement of infective virus particles is currently available. Genetically pure HBV stocks have not been available prior to the present invention. These limitations severely restrict efforts to provide HBsAg in improved amount and quality for the production of antibody suitable for more sensitive immunoassay, for passive immunization, and antigen for active immunization. Furthermore, the inability to passage the virus outside of humans or higher primates makes it impossible to obtain sufficient antigen for the production of a vaccine. The limited host range of HBV and its failure so far to infect tissue culture cells have drastically restricted study of the virus and have hindered development of a vaccine for the serious diseases that it causes.

Recent evidence strongly indicates a link between HBV and primary hepatocellular carcinoma. Epidemiological studies have indicated a high correlation of HBsAg or HBcAg in patients with primary hepatocellular carcinoma, Trichopoulos, D. et al., *Lancet*, 1978, 8102. More significantly, a strain of cultured hepatocellular carcinoma cells ("Alexander" cells) is known to produce HBsAg. These cells therefore contain at least part of the HBV genome. Further elucidation of the role of HBV in hepatocellular carcinogenesis and the molecular mechanisms of the carcinogenic transformation depends upon the development of suitable biological systems for maintenance and manipulation of the virus or its genome.

SUMMARY OF THE INVENTION

The invention provides, for the first time, a biological system for maintaining, modifying and replicating a genetically pure stock of an NP virus genome or a fragment thereof. The system provides means for making genetically pure viral components, such as coat and core proteins suitable for vaccines and for making viral DNA for use in studying the molecular biology of the viral infection and replication process. The latter is especially valuable because of its significance in understanding the induction of the chronic diseases NP-viruses typically cause, including certain auto-immune diseases and certain types of cancer.

The present invention is exemplified by the cloning and expression of HBV-DNA. Novel DNA transfer vectors are provided containing both the entire HBV genome and portions thereof. The transfer vectors are used to transform a suitable host, thereby permitting replication of the cloned viral DNA, or portions thereof, and also permitting the biological synthesis of viral proteins, including an immunologically active protein constituent of HBsAg, in desired amounts. An immunologically active protein constituent of HBsAg is useful as a vaccine for active immunization, and for the production of antiserum which in turn is useful for clinical screening tests and for providing passive immunity. A purified immunologically active protein constituent of HBsAg, designated the S protein, and fusion proteins thereof with a procaryotic protein fragment have been synthesized by a microorganism. The S-protein and derivatives thereof are useful as antigens to make a vaccine against HBV.

A novel DNA transfer vector comprising the entire HBV genome and a microorganism transformed therewith were placed on deposit in the American Type Culture Collection, 12301 Parklawn Drive, Rockville, Md. 20852, on May 23, 1979 in conjunction with the filing of the parent application. The deposited transfer vector is that designated pEco63 herein, with ATCC accession number 40009. The deposited microorganism *E. coli* HB101/pEco63, has ATCC accession no. 31518.

DETAILED DESCRIPTION OF THE INVENTION

Figure 1:
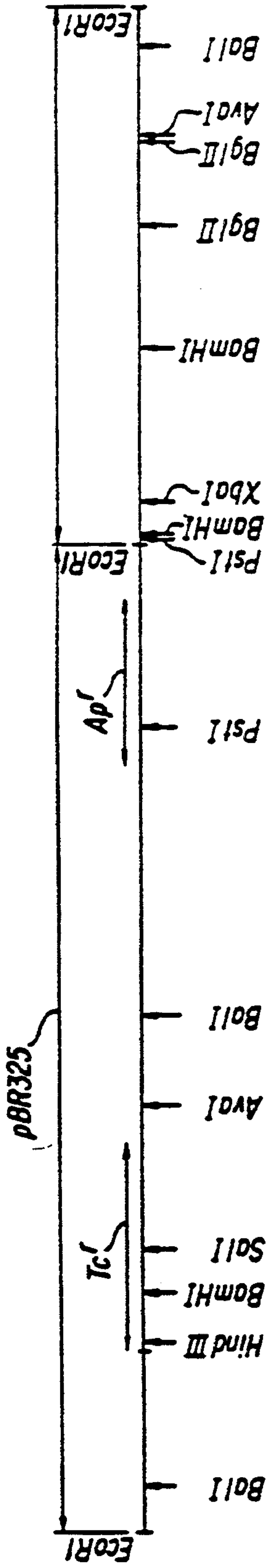

A novel biological system is provided for maintaining, replicating and modifying an NP-viral genome or cDNA thereof. The system is a combination of methods and compositions of matter that render NP-viruses amenable to a variety of research activities. The principal limitation is that at least a portion of the viral genome be isolatable either as viral genetic material or as viral mRNA. In general, the method entails isolating and purifying the viral genome or portion thereof, recombining the isolate with a DNA transfer vector, and transferring the transfer vector to a suitable host cell wherein the transfer vector is replicated and its genes expressed. Novel transfer vectors are thereby produced comprising all or part of the viral genome.

The NP viral genome may be either DNA or RNA. In the case of DNA, the entire genome or a fragment may be recombined directly with a transfer vector. In some circumstances, viral mRNA may be isolated from tissues or cells of infected individuals, whereby it would be possible to synthesize a cDNA copy of the viral mRNA. The cDNA would then be recombined with a DNA transfer vector. In the case of an RNA virus, cDNA reverse transcripts of the viral genome are readily obtainable, and would then be recombined with a DNA transfer vector.

Copies of the viral DNA, replicated in host cells descended from a single cell and containing a single copy of the viral genome or genomic fragment, are identical in sequence to the original copy and are therefore clones of the viral genome, or fragment. Expression of cloned viral DNA is accomplished by a variety of in vivo and in vitro methods. Expression in procaryotic host cells is accomplished by inserting the viral DNA in the middle of a translatable transfer vector gene, in proper orientation and reading frame, such that read-through translation or re-initiation translation occurs. In vitro translation can be carried out using known methods for DNA-directed protein synthesis (Zubay, G., *Ann. Rev. Genetics* 7, 267 (1973)). Where nontranslated intervening sequences are encountered, see, e.g., Crick, F.H.C., *Science* 204, 264 (1979), suitable eucaryotic host cells capable of correctly translating genes of this type may be chosen for the purpose of obtaining expression.

Further details of the system are described with reference to the cloning of HBV-DNA. The cloning of other NP-viruses will differ in respect to details and variations known in the art. For example, it will be understood that the selection of preferred restriction endonucleases for a given virus will be a matter of ordinary skill. Similarly, the choice of transfer vectors and host cells will be based on principles known in the art.

HBV-DNA may be obtained from Dane particles which are present in the plasma of certain human HBsAg carriers. Dane particles may be partially purified by differential centrifugation. Since much of the DNA extracted directly from Dane particles contains single-stranded regions, the DNA is initially repaired by filling the single-stranded gaps. A conventional DNA polymerase reaction may be employed, acting upon DNA extracted from the Dane particles. However, the preferred method is to exploit a DNA polymerase activity that is endogenous in the particles themselves, as described by Hruska, J. F. et al., *J. Virol.* 21, 666 (1977). In the preferred method, the DNA is first repaired, then extracted from the particles. If desired, radioactive label may be incorporated during the polymerase reaction.

For the purpose of cloning, the circular HBV-DNA must be cleaved internally at one or more sites to enable its subsequent covalent attachment to a DNA transfer vector. The attachment process is catalyzed by a DNA-ligase enzyme and is termed ligation. The internal cleavage may be carried out using non-specific endonucleases, many of which are known in the art, which catalyze the hydrolysis of the phosphodiester bonds of DNA at random sites on the DNA. Preferably, however, the cleavage should be carried out using one or more restriction endonucleases, which catalyze the hydrolysis of only those phosphodiester bonds located within certain deoxynucleotide base sequences known as restriction sites. See, Roberts, R., *Crit. Rev. Biochem.* 4, 123 (1976). A wide variety of restriction endonucleases is commercially available. The existence of a given restriction site in a given segment of DNA the size of the HBV genome is largely a matter of chance. Some sites may be frequently encountered, others not at all. We have found that HBV-DNA contains a single site for the restriction endonuclease EcoRI. Digestion of HBV-DNA by EcoRI converts the circular DNA to linear DNA without significant alteration of molecular weight. As a consequence of using a restriction endonuclease, all the linear digestion products have the same base sequence at their ends. Similarly, digestion by the enzyme BamHI produces two linear DNA fragments, which can be fractionated according to molecular length by gel electrophoresis. Digestion with both enzymes, EcoRI and BamHI, will produce three linear DNA fragments whose sizes determined by gel electrophoresis will permit certain inferences as to the relative locations of the EcoRI site and the two BamHI sites. By analyzing the effects of various combinations of restriction endonucleases on the sizes of fragments produced, it is possible to construct a restriction map of HBV-DNA which shows the relative locations of restriction sites with respect to each other. Such a map is shown in FIG. 1 for HBV-DNA.

By appropriate choice of restriction endonucleases, it is possible to transfer the entire genome of HBV, or any segment and overlapping combinations of segments, to a DNA transfer vector capable of replicating the transferred HBV-DNA in a suitable host organism.

The choices of transfer vector and host are interrelated and governed by certain practical considerations such as the desired end use and the relevant bio-hazard. For virus particle synthesis or for maximal rates of expression in some instances, eucaryotic host cells may be more suitable. The transfer vectors chosen must be capable of entering and replicating in the host. For rapid DNA replication, ease and safety of handling, for preservation of genetic purity and for pilot studies, a microbial host such as *Escherichia coli* is preferred. Numerous DNA transfer vectors are known for *E. coli.* Plasmid transfer vectors have been employed herein, merely for convenience.

Attachment of the HBV-DNA to a transfer vector requires opening the transfer vector circular DNA, preferably at a given site, followed by ligation of the linear HBV-DNA with the linear transfer vector DNA to form a circular recombinant transfer vector containing the HBV-DNA inserted in its nucleotide sequence at the site where it was originally cleaved. Preferably, for recovery of the inserted DNA sequent, subsequent to amplification, the ends of the transfer vector DNA and HBV-DNA are treated to provide a specific means for specifically removing the HBV-DNA from the recombinant transfer vector. One method of treatment entails the addition of double-stranded oligodeoxynucleotide "linker" molecules whose base sequence includes one or more restriction site sequences, Scheller, R. H. et al., *Science* 196, 177 (1977). A second method, termed "tailing", involves addition of oligo-G and oligo-C sequences at the ends of the endonuclease-treated plasmid, and viral DNAs, respectively, in a reaction catalyzed by terminal transferase. (It will be understood that base sequences in DNA refer to deoxyribonucleotides, while base sequences in RNA refer to ribonucleotides.) At the point of joining, a GGCC sequence is generated, which is a restriction site sequence specific for HaeIII. The inserted segment may be released from the plasmid by digestion with HaeIII (see, Villa-Komaroff, L. et al., *Proc. Nat. Acad. Sci. USA* 75, 3727 (1978)). The linker method enables the sequence at the joint between the two DNAs to be precisely defined. The tailing method produces a family of joined molecules. There is a one-third probability that a given clone, joined by tailing, will have the same translational reading frame as the transfer vector gene to which it is joined, which enables expression of the cloned gene by read-through translation from the transfer vector gene. There is also one-half probability that the inserted DNA will be joined in the same translation orientation, so that the composite probability that a given clone can be expressed is 1/6, see, Polisky, B. et al., *Proc. Nat. Acad. Sci. USA* 73, 3900 (1976); and, Itakura, K. et al., *Science* 198, 1056 (1977). Tailing is therefore preferred where expression is desired in the absence of evidence that the vector and the insert are in phase with respect to reading frame.

Transfer of the recombinant transfer vector to the desired host is accomplished by means appropriate to the individual host-vector pair. Plasmids are generally transferred to a microorganism host by transformation. The vector-containing host replicates the transfer vector in keeping with its own cell division with the result that proliferation of the host cells results in concomitant multiplication of the recombinant transfer vector. Host cells containing a particular recombinant insert can be identified by appropriate selection means. For example, insertion of an exogenous DNA fragment at the PstI site of plasmid pBR322 interrupts the gene conferring ampicillin resistance, so that host bacteria transformed by recombinant plasmids fail to be ampicillin resistant. Non-transformed cells can be screened by an appropriate transfer vector marker gene that is not affected by the insertion. The descendants of a single host cell containing a recombinant transfer vector are properly termed a clone of that cell strain. The inserted DNA segment carried by the transfer vector is thereby cloned. All copies derived therefrom have identical base sequences except for extremely rare random mutational changes. Host cells containing a recombinant transfer vector serve as an essentially inexhaustible source of supply for the cloned DNA.

Expression of the cloned DNA may be manifested by transcription, synthesis of mRNA corresponding to the cloned DNA, or by translation, synthesis of protein coded by the mRNA transcribed from the cloned DNA. The occurrence of transcription expression may be detected by the appearance of RNA capable of hybridizing specifically with the cloned DNA. Translation expression may be detected by the appearance of a function specific for the expected protein. For example, such a function may be an enzyme activity, a hormonal activity or an immunological specificity, that is characteristic of the protein coded by the cloned gene. In the case of viral gene products, the appearance of an immunologically reactive protein, such as HBsAg or HBcAg in the case of HBV, is the most likely possibility. Other sorts of specific binding reactions may be appropriate in certain circumstances. A sensitive in situ solid-phase radioimmunoassay has been developed for detecting expression from single colonies of transformed bacteria, Villa-Komaroff, L. et al., supra.

The above-described biological system for maintaining, replicating and synthesizing virus components provides for the first time a means for conducting clinical, biochemical and genetic research on viruses which can only be detected, directly or indirectly, in infected humans or higher primates. Such viruses, termed NP-viruses herein, include, but are not limited to, the Hepatitis B Virus, the "slow viruses" such as kuru and the agent implicated in the etiology of multiple sclerosis, and the xenotropic viruses, such as the C-type particles implicated in the causation of certain tumors. Little is presently known about such viruses, because of the lack of a suitable biological system for conducting experiments. Their public health significance cannot be underestimated, since their mechanism of action bears directly upon the mechanisms of cancer induction and on the development of auto-immune diseases. The present invention opens an entire new field for clinical, biochemical, immunological and genetic research on virus-related diseases. The system provides the following capabilities: the viral genome can be maintained and replicated in genetically pure form. Nucleotide sequence data can be obtained which will provide full information on the amino acid sequences of viral proteins, when correlated with information obtained by direct amino acid sequencing. Paradoxically, nucleotide sequences are easier to determine than amino acid sequences. Partial amino acid sequences, particularly at the ends of proteins, are useful to help establish starting points and reading frames. Labeled viral genetic materials can be used in hybridization experiments to locate and quantitate viral insertions in infected cell genomes. The viral proteins can be expressed in host cells, thereby permitting their characterization, production of antibodies against them, development of assays for their detection and measurement and the preparation of adducts and derivatives thereof. Vaccines can be prepared from the viral proteins. Such vaccines can be made available in the needed quantities and provide a substantial safety factor, since vaccines can be made by the described methods free of any contamination by intact or infectious virus particles. Antibodies against viral proteins are useful for clinical diagnosis of viral infection. The ability to make viral proteins in quantity makes it possible to study their biochemical characteristics and modes of action in contributing to the viral pathogenesis. The foregoing capabilities are illustrative only of the immediate benefits of the research made possible by the present invention. Longer term findings relating to subtle or unpredicted phenomena may also be expected to be of great significance.

The following examples are illustrative of the invention, as applied to HBV. The invention is not limited to its embodiment described in the examples. The system is applicable to any virus which cannot conveniently be maintained except by infection of humans or higher primates, but of which the genetic material, whether DNA or RNA, can be obtained, in whole or in part.

EXAMPLE 1

Cloning a viral DNA genome

Double-stranded circular HBV-DNA was obtained from Dane particles containing 25 μg DNA, as described by Hruska, et al., supra. The DNA was initially screened for sensitivity to restriction endonucleases by gel electrophoresis of the products of enzymic digestion. Gel electrophoresis fractionates nucleic acids according to their molecular length, Helling, R., et al., *J. Virol.* 14, 1235 (1974). Treatment of 100 ng DNA with EcoRI endonuclease (2 units) resulted in a single sharp band corresponding to about 3200 base pairs (bp) length. Similar treatment with BamHI endonuclease resulted in two fragments corresponding to about 1200 and 2000 bp length. Restriction endonucleases were obtained from New England BioLabs, Beverly, Mass. Units are defined by the manufacturer. All reactions using restriction endonucleases were carried out in buffers recommended by the manufacturer. From the number of fragments obtained in each case, it was inferred that HBV-DNA contains a single EcoRI site and two BamHI sites.

The DNA transfer vector selected was the plasmid pBR325 (Bolivar, F., *Gene* 4, 121 (1978), which is derived from plasmid pBR322 (Bolivar, F. et al., *Gene* 2, 95 (1977) and is capable of transforming *E. coli.* Plasmid pBR325 carries a gene conferring chloramphenicol resistance ($Cm^r$) and ampicillin resistance ($Ap^r$) on transformed cells. An EcoRI site exists in the $Cm^r$ gene such that an insertion of exogenous DNA at the EcoRI site renders the $Cm^r$ gene inoperative while leaving the $Ap^r$ gene unaffected. Recombinant clones of transformed *E. coli* are identified as chloramphenicol sensitive and ampicillin resistant, while non-transformed cells, sensitive to both chloramphenicol and ampicillin, fail to grow in the presence of either antibiotic. Clones transformed with non-recombinant pBR325 are identified as chloramphenicol resistant and ampicillin resistant. The microbiological methods used for growth and selection of recombinant strains were standard methods, described in *Experiments in Molecular Genetics* by Jeffrey H. Miller, Cold Spring Harbor Laboratory (1972).

For the insertion process, purified pBR325, 50 ng, and 300 ng. HBV-DNA were first treated together with EcoRI endonuclease, 10 units (10 μl total vol.) at 37° C. for one hour to yield linear plasmid DNA. The reaction mixture was heated to 65° C. for five minutes to inactivate EcoRI endonuclease.

The DNA was isolated from the reaction mixture by two cycles of ethanol precipitation. The precipitate was resuspended in 10 μl $H_2O$ to which a buffer concentrate was added to give 50 mM tri-HCl pH 8.0, 1 mM ATP, 10 mM $MgCl_2$ and 20 mM dithiothreitol. The mixture was pretreated by incubation at 37° C. for five minutes, followed by five minutes at room temperature. The mixture was then cooled in an ice bath and incubated with 1 unit T4 ligase (P-L Biochemicals, 11,000 units/ml) at 14° C. for 15 hours. The reaction mixture was added directly to a suspension of *E. coli* cells prepared for transformation by standard techniques. The host cell strain chosen was *E. coli* HB101, described by Boyer, H. W. & Rolland-Dussoix, D. *J. Mol. Biol.* 41:459–472 (1969). The choice of a particular strain was based upon convenience. Strain HB101 contains no other plasmids, is sensitive to chloramphenicol and to ampicillin and it is relatively easy to grow and maintain stocks of the organism.

Single colonies of transformed cells containing a recombinant plasmid, as judged by chloramphenicol sensitivity and ampicillin resistance, were grown in culture to provide a source of plasmid DNA. Cultures were grown in L-broth at 37° C. with aeration and harvested in late log or stationary phase. Alternatively, transformed cells were grown in a suitable minimal medium, as described by Bolivar, F., et al., supra, and Bolivar, F., supra, to an optical density at 660 nm of 1.0, using a 1 cm cuvette. Chloramphenicol, 170 μg/ml, was then added and the culture was incubated overnight. In either case, the plasmid DNA was isolated as supercoils from a cell lysate, using the method of ethidium bromide CsCl density gradient centrifugation described by Clewell, D. B. and Helinsky, D. R., *Proc.Nat. Acad.Sci USA* 62, 1159 (1969). Plasmid DNA prepared from transformed cells was treated with EcoRI endonuclease and fractionated by gel electrophoresis, as described. Single colonies were screened by the toothpick assay described by Barnes, W. M., *Science* 195, 393 (1977), to identify those bearing plasmids with large inserts. Two independently isolated recombinant plasmids containing insertions about 1200 bp in length were selected for subsequent studies. These were designated pEco-3 and pEco-63.

In similar fashion the BamHI fragments of HBV-DNA were separately cloned, using the BamHI site of plasmid pBR322 for insertion. Dane particle DNA (200 ng), labeled with $^{32}P$ by the nick translation method (Rigby, P. W. J., et al., *J.Mol.Biol.* 113, 237 (1977) was mixed with 200 ng unlabeled Dane particle DNA and 2 μl of 10-fold concentrated BamHI digestion buffer. The DNA was digested with 5 units BamHI endonuclease for 1 hour at 37° C. The mixture was heat treated at 65° C. for 5 minutes to inactivate the enzyme and the DNA recovered by two cycles of ethanol precipitation. The transfer vector, pBR322, was similarly digested with BamHI endonuclease and further treated with alkaline phosphatase as described by Ullrich, A., et al., *Science* 196, 1313 (1977). BamHI digested Dane DNA (250 ng) was incubated with 680 ng pBR322, treated as described, for 15 hours at 14° C. in a reaction mixture containing 50 mM tris-HCl, pH 8.0, 1 mM ATP, 10 mM $MgCl_2$, 20 mM dithiothreitol and 1 unit of T4 DNA ligase, following a pre-heating treatment as previously described. The ligation reaction mixture was used to transform *E. coli* and transformants were selected for ampicillin resistance and tetracycline sensitivity. A recombinant plasmid bearing the about 2100 bp BamHI fragment was designated pBam-132. A plasmid bearing a smaller fragment about 1100 bp was also obtained, designated pBam-69. Since the EcoRI site lies within the about 2100 bp BamHI fragment (see FIG. 1) it has been possible to clone the 1100 bp BamHI fragment from cloned EcoRI-treated HBV-DNA.

A preparation of HBV-DNA from pEco-63 was obtained, by specific cleavage to release the HBV-DNA, and inserted at the PstI site of pBR325. In this procedure, the plasmid pEco63 (3 μg) was first digested with EcoRI endonuclease, then treated with DNA ligase, under conditions previously described for the respective reactions. The resulting mixture of circular pBR325 and HBV-DNA is then incubated with PstI endonuclease and rejoined using DNA ligase. Both pBR325 and HBV-DNA have a single PstI site, so that the entire HBV-DNA can be inserted at the PstI site of pBR325. The resulting recombinant plasmid was designated pPst-7.

EXAMPLE 2

Identification of virus DNA in a recombinant plasmid

Figure 2A:
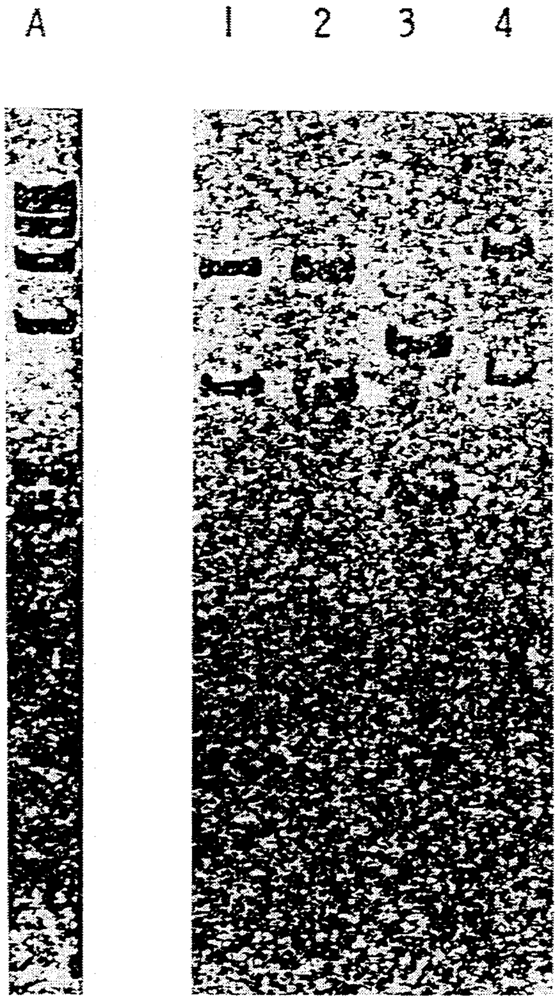
Figure 2B:
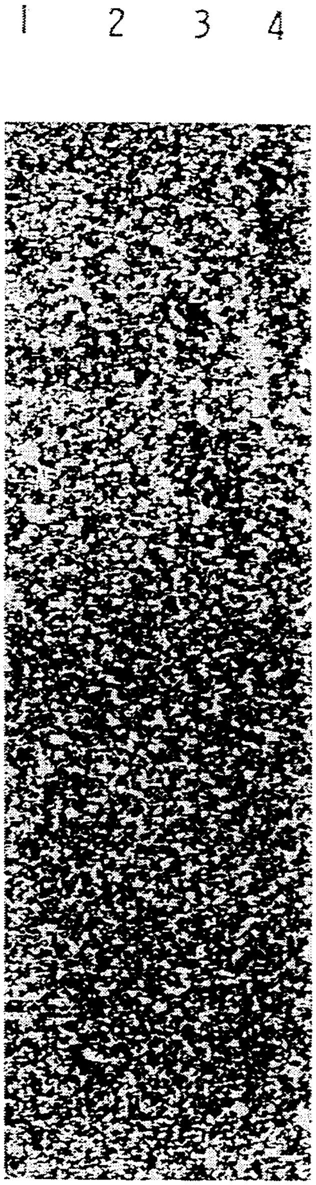

Recombinant plasmids pEco-3, pEco-63, pBam-132 and pPst-7 were prepared by growing transformed cells and isolating DNA therefrom, and separating host cell DNA from recombinant plasmid DNA by equilibrium density gradient centrifugation in the presence of ethidium bromide. Recombinant plasmid DNA was then treated with the restriction endonuclease specific for the respective insertion site. The DNA was fractionated by gel electrophoresis and analyzed by the method of Southern, E. M., *J.Mol.Biol.* 98, 503 (1975). In the Southern method, the DNA is first fractionated by agarose gel electrophoresis, then denatured in situ and transferred directly from the gels to nitrocellulose filters. The band pattern of the gels is thus replicated on the nitrocellulose filters. Denatured DNA binds to nitrocellulose filters. The filter-bound DNA is identified by hybridization with $^{32}P$-labeled DNA of known origin. In the case of HBV-DNA clones, $^{32}P$-labeled DNA from Dane particles was used as the hybridization probe. The results are shown in FIG. 2. Lanes 1, 2, 3 and 4 represent pEco-3, pEco-63, pBam-132 and pPst-7, respectively. FIG. 2A (bright lines on dark field) shows the gel electrophoretic pattern of the DNAs prior to hybridization. Two bands are seen in each case, visualized by fluorescence staining with ethidium bromide. The uppermost band being the linear transfer vector DNA, pBR325, in lanes 1, 2 and 4, and pBR322 in lane 3, the lower band being the putative HBV-DNA. (The smaller DNA fragments migrate downward, as the figure is oriented.) Lane A is a standard prepared from HindIII-treated bacteriophage DNA. FIG. 2B is an auto-radiogram of the nitrocellulose filter after hybridization with $^{32}$P-HBV-DNA. A band of hybridized DNA is observed in each case, corresponding with the putative HBV-cloned DNA, while very little $^{32}$P-DNA is observed hybridized to the plasmid DNA bands. The $^{32}$P-DNA hybridized to the plasmid was known to be slightly contaminated with pBR325, which probably accounts for the slight degree of hybridization observed with the plasmid bands. In this manner, all clones have been tested for identity. The four plasmids tested were thus shown to carry HBV-DNA.

Figure 2C:
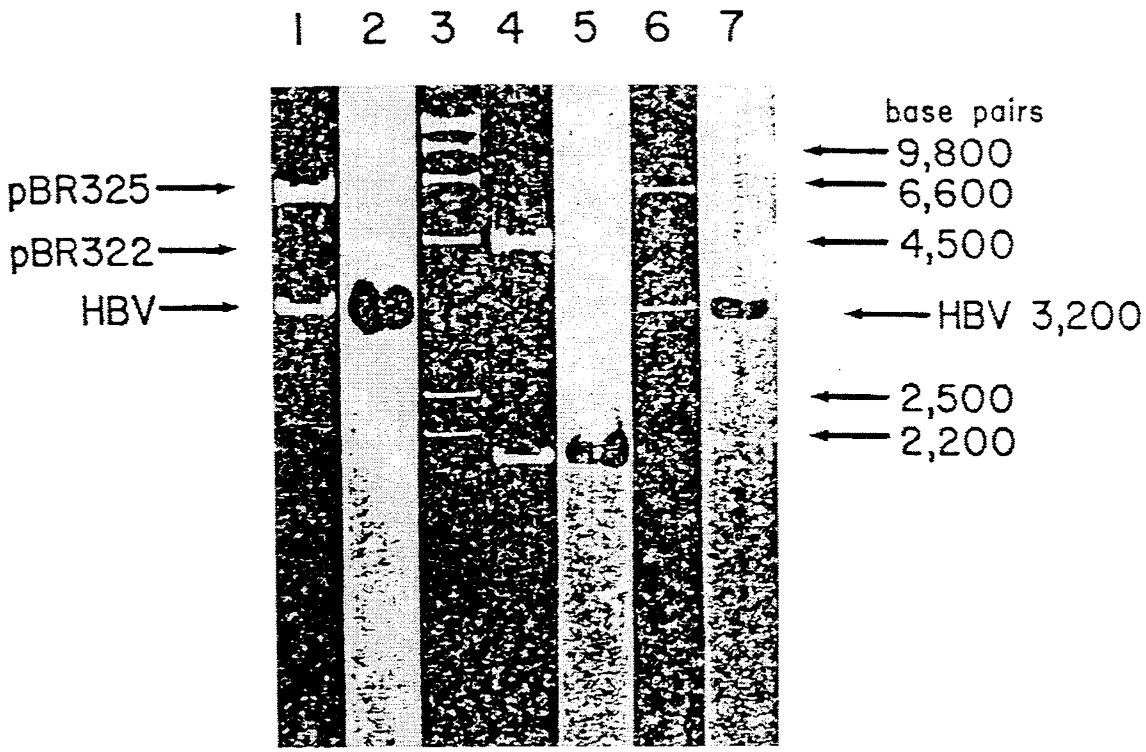

FIG. 2C shows the results of an independent experiment using an independently prepared sample of $^{32}$P-labeled Dane particle DNA as probe. Lane 1 shows pEco63 DNA digested with EcoRI endonuclease, visualized by ethidium bromide fluorescence staining (bright bands on dark field); Lane 2 shows hybridization of the DNA of lane 1 to $^{32}$P-labeled Dane particle DNA, visualized by autoradiography (dark band on light field); Lane 3 shows molecular weight standards prepared by HindIII digestion of λ DNA; Lane 4 shows pBam132 DNA digested with BamHI endonuclease; Lane 5 shows hybridization of lane 4 DNA with $^{32}$P-labeled Dane particle DNA; Lane 6 shows pPst7 DNA digested with PstI endonuclease; and Lane 7 shows hybridization of lane 6 DNA with $^{32}$P-labeled Dane particle DNA.

EXAMPLE 3

Transcription expression

Transcription expression was demonstrated by showing that mRNA isolated from host cells transformed by a recombinant transfer vector was complementary with viral DNA. The experimental method used herein was that of Alwine, J. C. et al., *Proc. Nat. Acad. Sci. USA* 74, 5350 (1977). In the Alwine et al. method, RNA fractionated by gel electrophoresis is transferred directly to a solid phase support, preserving the gel banding pattern. Hybridization to a $^{32}$P-labeled DNA probe is carried out on the solid phase support. The method is analogous to the technique described in Example 2 but differs in detail because RNA does not bind to nitrocellulose filters. In the method of Alwine et al. diazobenzyloxymethyl-paper filters are employed to bind RNA transferred from the electrophoresis gel. After binding the RNA, the derivatized paper is treated to hydrolyze excess diazo groups to prevent non-specific binding of the $^{32}$P-labeled probe.

The labeled DNA probe used in this example was cloned pEco-3 or pEco-63 DNA labeled with $^{32}$P during growth of the host strain. To eliminate hybridization between the pBR325 portion of the labeled probe and its mRNA, a 50-fold excess of unlabeled pBR325 was added to the hybridization mixture.

RNA was isolated from host cells carrying either pEco-3, pEco-63, pBam-69, pBam-132, pPst-7 or pBR325 grown to mid-log phase in 100 ml batches. Cells were collected by centrifugation for 10 minutes at 6000 rpm in a GSA rotor (DuPont Instruments, Newtown, Conn.). The pellet was resuspended in 2 ml of 10 mM tris, pH 7.6, 5 mM magnesium acetate and 10 mM KCl, then transferred to a tube containing 1 mg lysozyme. The cells were then quick-frozen, 0.25 ml sodium dodecylsulfate 10% (w/v) added, thawed and thoroughly mixed. Sodium acetate, 1M, pH 5.2, 0.25 ml, was added with mixing.

The RNA was extracted with water-saturated phenol, 2.5 ml, by intermittent mixing at 37° C. for a period of 30 minutes. The aqueous phase was removed and re-extracted with fresh water-saturated phenol. The aqueous phase was then extracted with ether. A centrifugation at 5000 rpm for 5 minutes was helpful to separate the phases. A gummy material at the interface was discarded. RNA was precipitated by addition of a ⅔ volume of 5M NaCl and 2.5 volumes of ethanol, incubated overnight at −20° C. The precipitate was collected by centrifugation at 10,000 rpm (HB4 rotor, DuPont Instrument Co., Newtown, Conn.) for 20 minutes at −20° C., washed once with ethanol and then redissolved in 4 ml of 10 mM tris, pH 7.4, 1 mM EDTA. The solution was centrifuged at 10,000 rpm in the HB4 rotor for 10 minutes at 0° C., and the pellet discarded. To the supernatant solution was added 8 ml of 4.5M sodium acetate, pH 6, to precipitate RNA preferentially at −20° C. for 8 hours. The precipitate was collected by centrifugation at 10,000 rpm for 20 minutes in the HB4 rotor at −20° C. The foregoing precipitation generally removed about 70% of the DNA. The precipitate was resuspended in 3.5 ml tris, 10 mM, pH 7.4, 1 mM EDTA, 7 ml sodium acetate and again precipitated. The final pellet was resuspended in 0.4 ml tris EDTA and stored frozen.

Figure 3A:
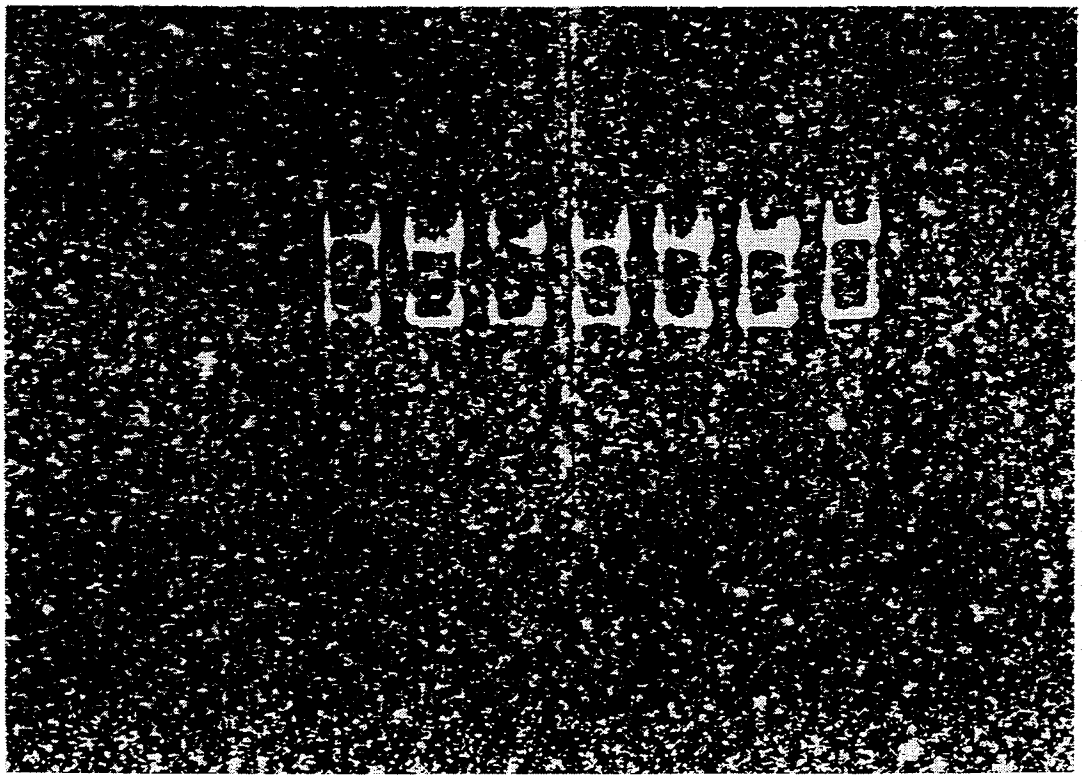
Figure 3B:
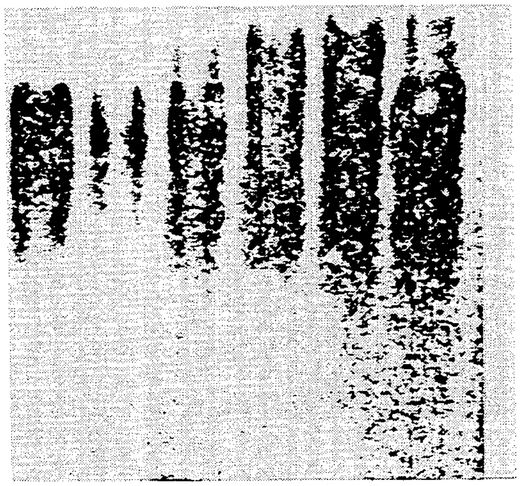

RNA, prepared as described, was fractionated by gel electrophoresis for hybridization analysis as described by Alwine et al., using 10 μg RNA per lane. The results are shown in FIG. 3A and FIG. 3B. FIG. 3A shows the gel electrophoresis results, as visualized by fluorescence staining. In every case, two major RNA bands are seen corresponding to 16S and 23S ribosomal RNA. FIG. 3B shows an auto-radiogram of $^{32}$P-HBV-DNA from pEco 63, $10^7$ cpm/μg, capable of hybridizing to RNA in the respective gels. Lanes 1–6 represent the results with RNA extracted from cells infected with the following plasmids: Lane 1, pBam-69; Lane 2, pBR325; Lane 3, pPst-7; Lane 4, pEco-63; Lane 5, pEco-3; Lane 6, pBam-132. Lanes A and B are standards of purified bacteriophage MS-2 RNA and *E. coli* ribosomal RNA, respectively.

It can be seen that hybridizable material was found in each case, and that the extent of hybridization was significantly greater in the case of the recombinant plasmids. Furthermore, in comparing the size of hybridizable material, it can be seen that the larger clones, pEco-63 and pEco-3, gave rise to a wider range of RNA sizes and to longer maximal length RNAs than did the shorter insertions, pBam-69 and pBam-132.

From the foregoing data it is clear that transcription expression of cloned HBV-DNA occurs in *E. coli.*

EXAMPLE 4

Nucleotide sequence of HBV-DNA

The sequence of the entire HBV genome was obtained from cloned HBV-DNA carried on plasmids pEco-3, pEco-63 or pPst-7 described in Example 1, by the method of Maxam, A. and Gilbert, W., *Proc. Nat. Acad. Sci. USA* 74, 560 (1977). The sequence is given in Table 1. The sequence is written as a linear sequence beginning at the EcoRl cleavage site. The sequences of both strands are shown, the upper sequence of each line reading from 5′ to 3′ left to right, the lower (complementary) sequence reading from 3' to 5', left to right. The abbreviations used indicate the bases of the deoxynucleotide sequence: A for Adenine, T for thymine, G for Guanine and C for Cytosine.

EXAMPLE 5

On the basis of the nucleotide sequence of HBV-DNA, as determined in Example 4, the location of a sequence coding for the S protein, an immunologically active protein constituent of HBsAg, was found. The first 19 amino acids of the N-terminal sequence and three amino acids of the C-terminal sequence of an immunologically active protein constituent of HBsAg are known from the work of Peterson, D. L., et al. (1978), supra. The smaller BamHI fragment of about 1,100 bp length was found to contain a nucleotide sequence coding for a sequence similar to the N-terminal 19 amino acids of the protein constituent of HBsAg, and also described by Peterson coding for the same three C-terminal amino acids, in phase with the N-terminal sequence and just prior to a TAA termination codon. The protein encoded by this sequence is 226 amino acids long and has a molecular weight of 25,398, in satisfactory agreement with the mass (22,000–24,000) determined by sodium dodecyl sulfate gel electrophoresis of other protein constituents of HBsAg isolated by Gerin, J. L. and Shi, J. W. K., or by Peterson, et al. (1978), supra. The 226 amino acid protein described herein is designated the S protein. For reference purposes, the reading frame of the S protein coding sequence is designated Frame 1. Frames 2 and 3 are shifted forward 1 and 2 nucleotides, respectively. The relationships are illustrated by the following diagram, based on the first 9 nucleotides of the S protein coding sequence:

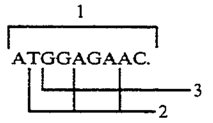

Figure 4:
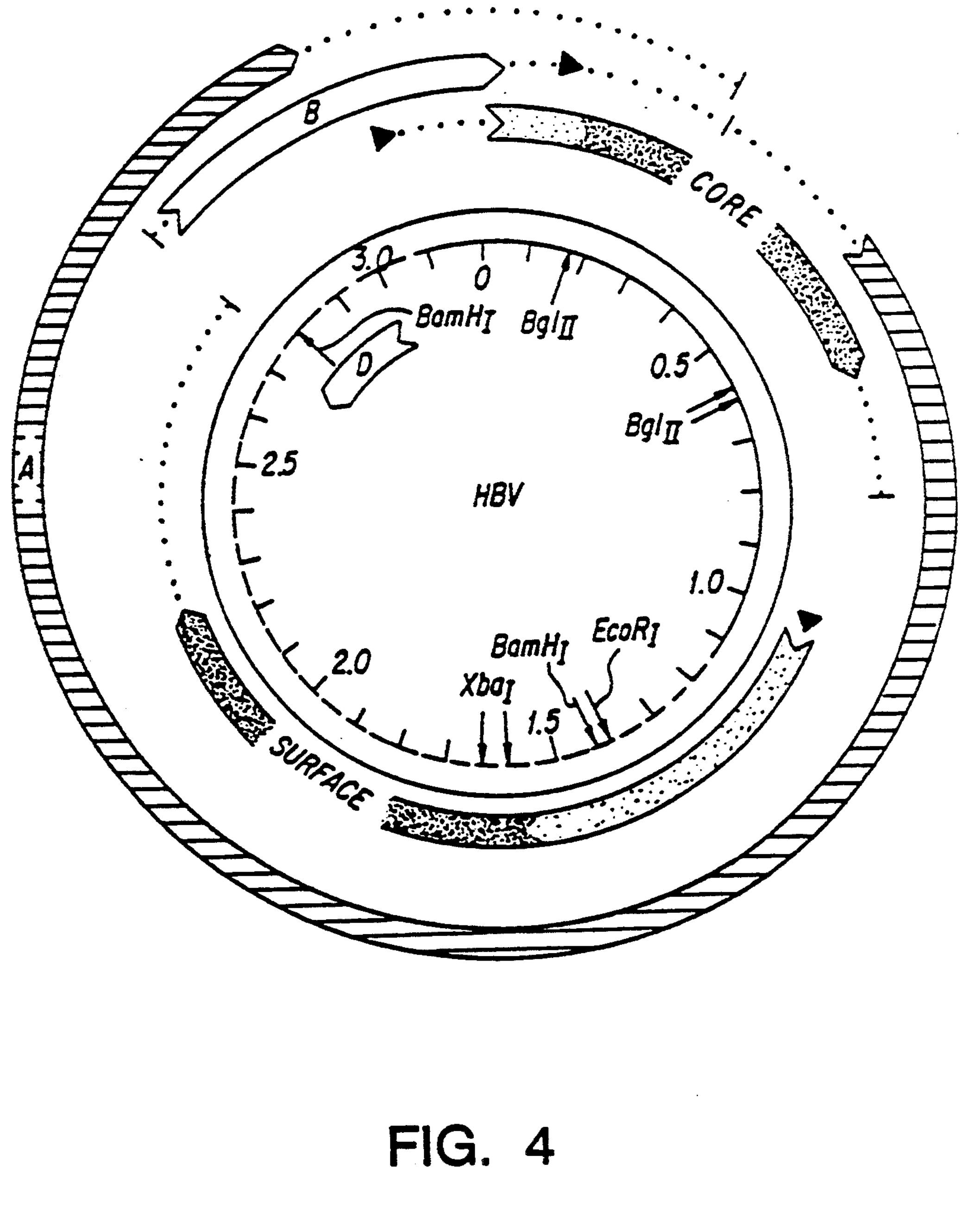

The amino acid composition of the S protein, predicted from the nucleotide sequence, is in very close agreement with that reported for the protein constituent of HBsAg, described by Peterson et al. (1978), supra. However, the N-terminal amino acid sequence differs from that previously reported, by having a leucine residue a position 15, instead of a serine. The map location of the S protein coding region is shown in FIG. 4.

Because of the prevalence of intervening sequences in eucaryotic genes, Robertson, M. S., et al., *Nature,* 278, 370 (1979), it is not possible to presume the colinearity of a gene with the amino acid sequence of the protein product. There is, however, no evidence for an intervening sequence in the S protein gene, since the molecule predicted by the DNA sequence closely approximates the characteristics of an immunologically active constituent of the surface antigen. Any intervening sequence(s) would have to be small (<150 bases); most intervening sequences in structural genes are longer. The N-terminal and C-terminal ends of the molecule are in phase, thus any intervening sequence must also maintain the phase. Therefore, the conclusion is justified that the identified S protein coding region is colinear with the mRNA.

The complete amino acid sequence of S protein, based on the DNA nucleotide sequence, is given in Table 2. Standard abbreviations used in protein chemistry are used to denote the amino acids. The starting point identified for the S-protein is the methionine residue coded by nucleotides 1564–1566 in Table 2. As indicated in FIG. 4 and in Table 2, the S-protein coding region includes a substantial region coding for an additional N-terminal sequence of amino acids beginning at the methionine coded by nucleotides 1042–1044 or alternatively the methionines coded by nucleotides 1075–1077 or nucleotides 1399–1401. Protein encoded by these regions has not been recognized as a component of HBV. However, such proteins may serve a biological function as yet unknown in the infection process. Additionally, the proteins initiated from the described starting points are useful S-protein derivatives having N-terminal amino acid sequences coded by naturally occurring nucleotide sequences, which have greater molecular weight and higher antigenicity than S-protein itself. These S-peptide analogs are useful in eliciting antibodies directed against S-protein, for immunization and for assay purposes.

There are two Tac I restriction sites located near either end of the S-protein coding region. The smaller Bam HI fragment was treated with Tac I endonuclease to provide blunt ends. Hind III linkers were attached by blunt end ligation to the blunt ends of the Tac I fragment (Sugino, A., et al., *J. Biol. Chemistry* 252, 3987 1977). The fragment was then inserted into the expression plasmid ptrpE30, derived from plasmid ptrp ED50 (Martial, J., et al., *Science* 205, (1979)). Plasmid ptrpE30 contains the operator, promoter attenuator and ribosome binding sequences of the tryptophan operon, together with a nucleotide sequence coding for seven amino acids of the trp E protein followed by a Hind III site in the direction of normal translation. This plasmid was used for convenience in providing a known reading frame compatible with expression of S-protein, upon insertion at the Hind III site.

The expression plasmid ptrp E30 was pretreated with HindIII endonuclease. The treated S-protein coding fragment was then inserted into the treated plasmid by means of DNA ligase catalyzed joining reactions. The HindIII site of ptrpE30 is known from sequence data to provide a reading frame in phase with the inserted S-protein coding sequence. Transformation of *E. coli* HB101 led to expression of a trp E-S protein fusion protein under tryptophan operon control, and inducible with β-indolylacrylic acid, as next described. This strain was designated *E. coli* HB101/ptrp E30-HBsAg.

Bacterial cells transformed by ptrpE30/HBsAg were grown in a standard minimal medium (M9) supplemented with leucine, proline, vitamin B1 and ampicillin, at 37° C. In early log phase, the trp operon was induced by addition of β-indolylacrylic acid (30 μg/ml of medium). Control cultures were left uninduced. After 3 more hours of growth, 1.5 ml of cells were radioactively labeled by addition of 20 μCi $^{35}$S-L-methionine and incubation for 10 minutes. The cells were then collected by centrifugation, washed and resuspended in 250 μl of buffer containing glycol 10% (v/v), β-mercaptoethanol 5% (v/v), and SDS 2.3% (w/v) in 0.0625M tris pH6.8. The suspension was boiled for 5 minutes, then applied to a 10% (w/v) SDS-polyacrylamide gel and fractionated by electrophoresis. The protein bands were visualized by autoradiography. The results are shown in FIG. 5.

Individual isolates of transformed HB101ptrp E30/HBsAg were designated p126, p135, p146, p150, p155 and p166, respectively. The proteins of induced and non-induced cultures are shown side by side for comparison, labeled, e.g. p126ind, or p126, respectively. Standards include cells transformed with ptrp E30 lacking an insert, and a mixture of proteins of known size: Bovine serum albumin, ovalbumin, carbonic anhydrase and lysozyme, having molecular weights (M.W.) of 69,000 ("69K"), 43,000 ("43K"). 30,000 ("30K") and 14,300 ("14.3K") respectively.

Figure 5A:
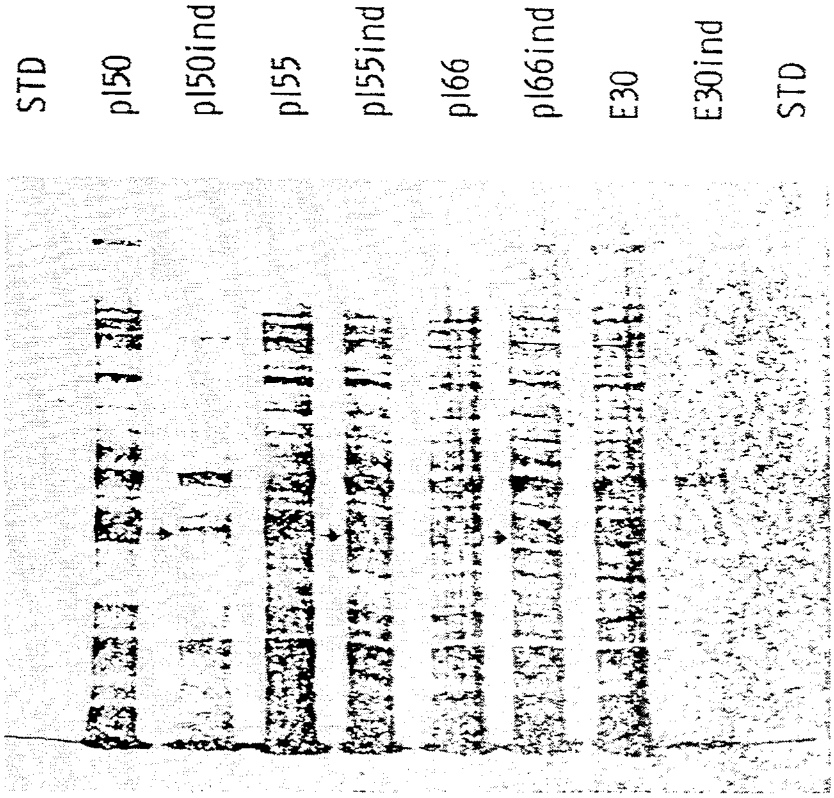
Figure 5B:
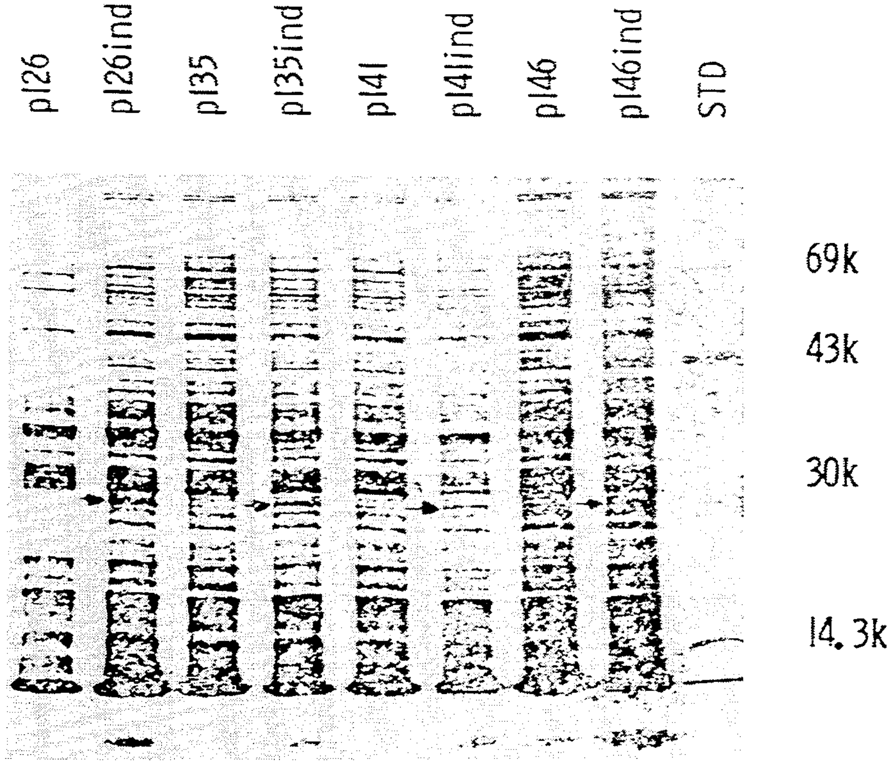

The expression of the trpE-S protein fusion protein was demonstrated by the apperance of bands, unique to induced cultures, indicated in FIG. 5 by the small arrows, of a protein having a M.W. approximately 27,000. The calculated M.W. of the trpE-S protein fusion product is 27,458. The fusion protein includes 7 amino acids from the N-terminus of the trp E protein, and 12 amino acids coded by the HindIII linker and the nucleotides lying between the TacI site and the start of the S-protein coding region. The amino acid sequence of the fusion protein is: Met-Gln-Thr-Gln-Lys-Pro-TrpE-Thr-Pro-Ser-Leu-Ala-Arg-Thr-Gly-Asp-Pro-Val-Thr-Asn-S, where S stands for the amino acid sequence of the $^{12}$S-protein.

Expression of the S-protein coding region was detected by its immunochemical reactivity with antibody to HBsAg, in a competitive radioimmune assay with labeled HBsAg (AUSRIA, trademark Abbott Laboratories, North Chicago, Ill.). Expression is also detected by immunoprecipitation. A culture of *E. coli* HB101/ptrp E30-HBsAg is induced with $\beta$-indolyl acrylic acid, and 3 ml samples pulse labeled with 2 $\mu$Ci of $^{14}C$-labeled amino acids or $^{35}S$-methionine for a constant time, at various intervals after induction. Samples from the Zero and 4 hour-induced cultures are immunoprecipitated after reaction with antibody to HBsAg, using formaldehyde treated *Staphylococcus aureus* to collect the antigen-antibody complexes, as described by Martial, J. A., et al., *Proc. Nat. Acad. Sci. USA* 74, 1816 (1977). The precipitated proteins are solubilized and fractionated by electrophoresis in SDS polyacrylamide gels. The results show that immunoprecipitable protein appears in substantial amount only after induction, confirming the expression of the S-protein coding region under tryptophan operon control, and confirming the immunological reactivity of S-protein with antibodies to HBsAg.

The expression of S-protein by individual bacterial colonies is detected by a modification of the polyvinyl disk method of Broome, S. and Gilbert, W., *Proc. Nat. Acad. Sci. USA* 75, 3727 (1978), a disk of polyvinyl that has been washed thoroughly is floated on a solution of unlabeled IgG (in this case comprising antibody to HBsAg) at a concentration of 10–60 $\mu$g/ml in 0.2M $NaHCO_3$, pH 9.2 for 3 minutes. The disk is then washed 2 times in wash buffer (10 mg/ml gelatin, 1% serum (human, rabbit or guinea pig) 0.1% NP40, 0.02% $NaN_3$ in phosphate-buffered saline). The disk is then applied to an agar plate containing either lysed bacterial colonies or small liquid samples that have absorbed into the agar. The lysis of bacterial colonies can be achieved in any one of three ways:

1) exposure to $CHCl_3$ in a desiccator for 10–20 minutes,
2) transfer of bacterial colonies to an agar plate containing lysozyme, EDTA and Tris-HCl pH 9,
3) overlay the agar plate containing colonies with a lysozyme, EDTA, Tris-HCl, 10% wash buffer and 1% agarose solution. After the overlay solidifies, the coated polyvinyl disk can be applied directly.

All three methods appear to possess similar sensitivity. The overlay technique has the advantage of being able to recover bacteria from positive colonies after the lysis procedure. After a 1–4 hour incubation at 4° C. the polyvinyl disk is again washed 2 times in wash buffer. The polyvinyl disk is now incubated with 2 ml of $^{125}I$-IgG (anti-HBsAg) in wash buffer ($2\times10^6$ cpm/ml) overnight at 4° C. The polyvinyl disk is washed 2 times at 42° C. in wash buffer for 15 minutes apiece, then washed 2 times in distilled water at room temperature. The disk is then exposed to x-ray film at −70° C. for 18–48 hours. Areas that possess antigen appear as dark spots on the developed x-ray film. Colonies that possess antigen are identified as expressing the S-protein coding region. Cultures are grown from selected colonies for the purpose of producing the S-protein on a large scale. The trp E-S protein fusion product is purified from(cell-)lysates by conventional means, including gel filtration and affinity chromatography.

EXAMPLE 6

Bacterial Synthesis of S-Protein

The expression product of Example 5 is a fusion protein comprising S-protein and a 19 amino acid N-terminal sequence derived from the trp E protein (first 7 amino acids from the N-terminus), the HindIII linker (next 3 amino acids) and that portion of the HBV genome between the TacI site and the methionine initiating the S-protein (9 amino acids). For many applications, including vaccination of humans, it is preferred to achieve synthesis of S-protein itself, or one of its naturally coded derivatives, as shown in Table 2. It is technically feasible to remove the nineteen amino acid N-terminal sequence by limited treatment with an exopeptidase (aminopeptidase), however the yield of S-Protein would be expected to be low.

Expression of S-protein per se can be accomplished by modifying both the expression plasmid and the S-protein coding fragment, to remove from the former the nucleotides coding for the host portion of the fusion protein, and to remove from the latter any nucleotide preceding the start codon of the S-protein structural gene. Any expression plasmid may be employed, preferably one having an insertion site close to the beginning of translation, such as ptrp E30 or pBH20 (Itakura, et al., *Science* 198, 1056 (1977).

Treatment to remove short nucleotide segments is accomplished using exonucleolytic enzymes. A preferred enzyme is T4 polymerase, which, in the absence of added deoxynucleoside triphosphates, catalyzes 3′ to 5′ exonucleolytic digestion of double-stranded DNA, Englund, P. T., *J. Biol.Chem.* 246, 3269 (1971). The extent of digestion is controlled by selection of proper temperature, reaction time and amount of enzyme, according to principles well known in the art. Experimentation will be necessary in each instance, since optional reaction conditions must be determined for each lot of enzyme and for each DNA to be modified. By these means, the extent of digestion can be controlled. Termination of digestion at a predetermined stopping point is achieved by including a single deoxynucleoside triphosphate in the reaction mixture, corresponding to the desired stopping point. For example, in the presence of dATP, the DNA is digested 3′–5′ until the polymerase reaches a dA residue, at which point further net digestion ceases. Several cycles of digestion, each with its predetermined stopping point, can be carried out in sequence, to construct DNA molecules having a predetermined end point. Exonucleolytic digestion with T4 polymerase affects only the strands having 3′ termini. The complementary strands remain as unpaired single stranded tails, which must be also removed. S1 nuclease is the preferred enzyme for the purpose. The product of combined treatment with T4 polymerase and S1 nuclease is blunt-ended, double-stranded DNA.

The above-described treatments can be used to treat an existing expression plasmid to remove the nucleotides coding for the host portion of the fusion protein. The essential elements to be preserved are termed the expression unit. the expression unit includes a promoter and a ribosomal binding site capable of acting in the host organism. As a practical matter, it is not necessary to remove precisely the nucleotides coding for the host portion of the fusion protein. The relationship between the ribosomal binding site and the start codon (AUG) is such that the start codon may be located anywhere within 3 to 11 nucleotides of the ribosomal binding site, Shine et al., *Proc. Nat. Acad. Sci. USA* 71, 1342 (1974); Steitz, J., et al., *Proc. Nat. Acad. Sci. USA* 72, 4734 (1975). In this 3–11 nucleotide region, the first AUG to be encountered sets the reading frame for translation. In the case of ptrpE30, described in Example 5, the removal of a minimum of 23–29 nucleotides from the HindIII site provides a site for insertion into an expression unit under tryptophan operon control.

The digestion of ptrpE30 by HindIII endonuclease is carried out under conditions essentially as described in Example 1 for cleavage of plasmid DNA with restriction enzymes. The treated DNA is recovered from the reaction mixture by two cycles of ethanol precipitation. In one optimized T4 polymerase digestion reaction, 15 μg of DNA is resuspended in $H_2O$ and a solution of concentrated salts is added to provide a reaction mixture containing 70 mM Tris pH 8.8, 70 mM $MgCl_2$, 10 mM dithiothreitol and 13.75 units of T4 polymerase (P-L Biochemicals, Milwaukee, Wis.) in a total volume of 250 μl. The reaction mixture is incubated 3.3 minutes at 37° C. The reaction is terminated by rapidly transferring the incubation mixture to an ice bath, then inactivating the enzyme by 5-minute heat treatment at 65° C. The DNA is recovered by ethanol precipitation. S1 nuclease treatment is carried out as described by Ullrich, A., et al., supra.

In similar fashion, the Tac I fragment of HBV-DNA comprising the S-protein coding region, described in Example 5, is treated with T4 polymerase to remove approximately 30 deoxynucleotides from each 3′ end. BamHI linkers are added by blunt end ligation. The linkers have the sequence 5′-CCGGATCCGG-3′ on one strand and its complementary sequence on the other. Treatment with HpaII exonuclease, which cleaves the sequence CCGG to yield CGG, yields a DNA fragment which may be joined to any site having a 5′-terminal CG, for example HpaI cut DNA or ClaI cut DNA. A partial restriction map of the Tac I fragment is:

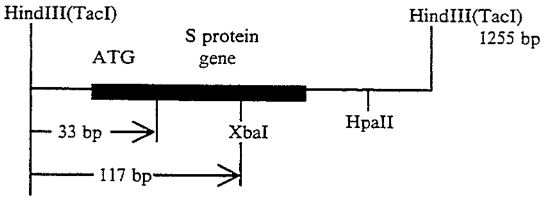

The TacI fragment, treated as described, is readily inserted into ptrpE30, also treated as described, and similarly provided with a HpaII—specific linker, in a DNA ligase catalyzed reaction as described by Valenzuela, et al., *Nature* 280, 815 (1979). Bacterial cells are transformed with the insert-bearing plasmid. Transformants are selected by resistance to ampicillin as described in Example 5. Cultures grown from single-colony isolates are induced with β-indolylacrylic acid, and pulse-labeled with $^{35}S$-methionine as described in Example 5. The labeled proteins are visualized by gel electrophoresis and autoradiography. The clones yielding protein bands in the 27,000 M.W. region are highly likely to be synthesizing S-protein, without a leader sequence.

If removal of the host protein coding region of the vector DNA is incomplete, there is a 1/6 chance that the inserted DNA will be expressed as a fusion protein. However, if too many nucleotides are removed from the vector DNA, it is probable that no protein will be formed coded by the insert DNA, while if the treated insert is too long, such that more than 11 nucleotides separate the ribosomal binding site from the start codon, little or no protein will be formed. Only if the vector retains part of its coding sequence, or the insert treatment has removed part of the S-protein coding region, will there be any possibility of incorrect protein synthesis. Therefore, identity of the protein made by a given clone is obtained by end group analysis, for example, by Edman degradation, to confirm the N-terminal sequence Met-Glu-Asn-Ile of S-protein. The correct plasmid construction is confirmed by DNA base sequence analysis (Example 4). Proof of structure of the expressed S-protein is accomplished by complete amino acid sequence analysis. True S-protein, synthesized by a bacterial strain, is purified by standard methods, such as gel filtration and affinity chromatography, and further characterized by immunochemical tests and tryptic digest analysis.

Purified S-protein is immunogenic and cross-reactive with antibody to HBsAg. The amino acid sequence, determined by the base sequence of the S-protein coding region is as follows:

⊖GluAsnIleThrSerGlyPheLeuGlyProLeuLeuValLeuGlnAlaGlyPhePhe
LeuLeuThrArgIleLeuThrIleProGlnSerLeuAspSerTrpTrpThrSerLeu
AsnPheLeuGlyGlySerProValCysLeuGlyGlnAsnSerGlnSerProThrSerAsnHis
SerProThrSerCysProProIleCysProGlyTyrArgTrpMetCysLeuArgArg
PheIleIlePheLeuPheIleLeuLeuLeuCysLeuIlePheLeuLeuValLeuLeuAsp
TyrGlnGlyMetLeuProValCysProLeuIleProGlySerThrThrThrSerThrGly
ProCysLysThrCysThrThrProAlaGlnGlyAsnSerMetPheProSerCysCysThr
LysProThrAspGlyAsnCysThrCys IleProIleProSerSerTrpAlaPheAla
LysTyrLeuTrpGluTrpAlaSerValArgPheSerTrpLeuSerLeuLeuValProPhe
ValGlnTrpPheValGlyLeuSerProThrValTrpLeuSerAlaIleTrpMetMetTrp

-continued

TyrTrpGlyProSerLeuTrySerIleValSerProPheIleProLeuLeuProIlePhePheCysLeuTrpValTyrIle.

Adaptation of the described techniques in combination with methods known in the art makes it feasible to construct a family of S-protein derivatives of the general formula $$X-\overset{\overset{O}{\|}}{S}-Y$$

wherein S is the amino acid sequence of the S-protein, X is an amino acid, peptide, protein or amino protecting group, including but not limited to the naturally coded amino acid sequences shown in Table 2, and also including peptides composed primarily of aromatic amino acids such as tyrosine, phenylalanine and tryptophan, said peptides being less than about 4 amino acid residues in length, as described by Sela, M., *Science* 166, 1365 (1965) and Sela, M., *Cold Spring Harbor Symposium on Quantitative Biology*, Vol. 32 (1967), having the property of increasing the antigenicity of proteins to which they are attached, and Y is an amino acid, peptide, protein or carboxyl protecting group in ester or amide linkage, including but not limited to the peptides composed of aromatic amino acids already mentioned. The S-protein has a molecular weight of 25,398. The derivatives will therefore have molecular weights greater than 25,398. The described S-protein derivatives have enhanced antigenicity and stability to proteolytic digestion. The derivatives are therefore useful as antigens for vaccination and for assay purposes.

Various amino protecting groups known in the art are suitable for use in making derivatives of the S-protein and peptide derivatives thereof. The choice of a suitable amino protecting group depends upon such factors as the nature of the amino acid to be protected, relative ease of removal, convenient reaction conditions such as solvent, temperature, etc. Suitable amino protecting groups include the benzyloxycarbonyl (carbobenzoxy) group, substituted carbobenzoxy or other urethane protecting groups, the trifluoro acetyl group, the phthalyl (or phthaloyl) group, the diphenylmethyl (benzhydryl) group, the triphenylmethyl (trityl) group, the formyl group, lactams, Schiff bases and N-amines, the benzylsulfonyl group, the trityl sulfenyl group and the aryl sulfenyl group. Commonly used amino protecting groups include the tert-butyloxycarbonyl group, the o-nitrophenyl sulfenyl group and the tosyl group. Reference is made to standard works on peptide chemistry such as Bodanszky, O., et al., *Peptide Synthesis*, Ch. 4, Interscience Publ. (1966); Schroeder, *The Peptides*, Vol. 1, pp. xxiii-xxix, Academic Press (1965); and *Protective Groups in Organic Chemistry* (J. F. W. McOmie, ed.), Plenum Press (1973).

Suitable carboxyl protecting groups known in the art include lower alkyl esters, phenyl-substituted lower alkyl esters, e.g., benzyl and benzhydryl esters, p-nitro benzyl esters, p-methoxybenzyl esters, phthalimidomethyl esters, t-butyl esters, cyclopentyl esters, methyl thioethyl esters, trimethyl silyl groups, and hydrazides. The choice of particular groups depends upon such variables as previously noted for choice of amino protecting groups. Commonly used carboxyl protecting groups are methyl, ethyl, propyl, t-butyl and benzyl.

Other functional groups, such as —OH and guanidino groups, may be protected by known methods, if desired.

Synthesis of the described S-protein derivatives is accomplished as described by Sela, et al., supra, or by modifications of the recombinant DNA techniques described in Example 1–6, making use of appropriate restriction sites for cleavage of the DNA near the desired starting point, and selectively removing short end segments using T4 polymerase. In cases where restriction endonuclease cleavage yields a shorter product than desired, the desired deoxynucleotide sequence can be provided by chemical synthesis. (See, e.g., Goeddel, D., et al., *Nature* 281, 554 (1979)). The scope of possible S-protein derivatives is not limited to those peptides of the naturally coded sequence that are initiated with a methionine residue, but includes all possible subsequences of the naturally coded sequence shown in Table 2.

In addition, glycosylated derivatives of the S-protein are antigenic and are useful for production of antibodies. The expected glycosylation sites are asparagine residues in the subsequence -Asn-M-(Ser) or (Thr)-, where M is any amino acid. There are three such sites, at amino acid positions 3, 59 and 146 of the S-protein. In addition, there are two such sites within the naturally coded sequence providing useful S-peptide derivatives, thereby providing for glycosylated derivatives as well.

EXAMPLE 7

In Vitro Synthesis of S-Protein

The expression of the S-protein coding region is carried out in Vitro using the DNA-directed protein synthesis system described by Zubay, G., supra. The DNA used in the synthesis is either the recombinant plasmid ptrpE30/HBsAg or the modified recombinant plasmid described in Example 6 for expression of S-protein. In addition, restriction endonuclease cut fragments of HBV-DNA, such as the Tac I fragment including the S-protein coding region, may be employed in the Zubay system. One or more of the amino acids provided in the system is radioactively labeled, in order to permit a sensitive assay for the product protein. Synthesis of S-proteins is detected by the binding of radioactively labeled material to anti-HBsAg antibody or anti-S-protein antibody, in any of the assay systems previously described.

EXAMPLE 8

The HBV-DNA and restriction fragments thereof are cloned in a bacteriophage transfer vector. For this purpose, the phage λ Ch16A is suitable, Blattner, F. R., et al., *Science* 196, 161 (1977). The phage contains a single EcoRI site, located in a lac5 substitution. Insertion into the lac5 region provides a useful selection technique: when the chromogenic substrate 5-chloro-4-bromo-3-indolyl -β-D-galactoside (XG) is included in the plating medium, λCh16A gives vivid blue plaques while λ Ch16A bearing an insert in the EcoRI site gives colorless plaques when plated on a $Lac^-$ bacterial host. Furthermore, the EcoRI site provides an insertion locus near a functional operator-provided region, suitable for expression of coding regions as fusion proteins bearing N-terminal portion of the β-galactosidase gene.

EXAMPLE 9

Identification of core antigen coding region

The HBV-DNA nucleotide sequence read in phase 2 provides an open region of 666 bp length bounded by a termination codon (TAG) and an initiation codon (ATG). An open region is one containing no termination codons in phase. The 555 bp region is the largest such open region in phase two of the HBV genome. An initiation sequence, TATACAAG, was observed prior to the ATG start codon, beginning at position 93 consistent with the conclusion that the region is a coding region for a protein. (See E. B. Ziff, et al. *Cell* 15, 1463 (1978), and F. Gannon, et. al., *Nature* 278, 428 (1979). The molecular weight of the encoded protein is 21,335, consistent with the estimated M. W. of 21,000 derived from gel electrophoresis, (See also Gerin, J. L. and Shi, J. W. K., supra.

Significantly, the amino acid sequence of the encoded protein includes an extensive region of predominantly basic amino acids in the C-terminal region of the protein. The encoded protein will therefore bind tightly to DNA, in a manner similar to a protamine, and consistent with the behavior expected for the core protein of a virus.

The encoded protein has been further identified as HBcAg by the existence of a single internal methionine residue. Cleavage of the encoded protein at this methionine residue would yield two fragments having about 35% and 65%, by weight, of the intact protein. Cleavage of isolated HBcAg by CNBr yields fragments of approximately 40% and 60%, by weight, of the intact protein, within experimental error of the predicted sizes (J. L. Gerin and J. W. K. Shi, personal communication).

On the basis of the predicted M.W., amino acid sequence consistent with known functional properties, and presence of a correctly placed internal methionine residue, the coding sequence for HBcAg has been identified. The predicted amino acid sequence of HBcAg is given in Table 2 and the map location on the HBV genome is shown in FIG. 4. The map in FIG. 4 shows a possible alternative start codon at position 2, which could provide an earlier initiation point and a somewhat longer amino acid sequence. The likelihood that the earlier start codon is actually utilized in vivo is reduced by the fact that the ATG codon at position 93 is preceded by an 18S ribosome binding site sequence, whereas no such sequence precedes the alternative start codon at position 2.

The expression of HBcAg in *E. coli* is obtained by conventional insertion of a restriction fragment containing the core antigen coding region into an expressed bacterial operon located in a transfer vector, in correct reading frame and orientation. Selection of the plasmid of choice is based upon considerations of operating convenience and yield. For example, insertions in the tryptophan operon are capable of providing high yields of expression product, as shown in Example 5. Insertions in the β-lactamase operon of pBR322 provide a protein that may be extracted from the periplasmic region of the cell, for greater ease of purification, and may prevent death of the host cell should the expression product be toxic. Given the known reading frame for the HBcAg gene, an expression plasmid having an insertion site in the correct reading frame is selected. Alternatively, the end to be inserted proximally to the operon is tailored by selective removal or addition of 1-2 nucleotides, using known techniques, to provide correct phasing of the reading frames of the operon and the insert.

EXAMPLE 10

Identification of additional proteins coded by HBV-DNA was facilitated by analysis of the nucleotide sequence. The distribution of termination codons in reading frame number 3 indicates an open region capable of coding for a large protein of molecular weight up to 95,000, hereinafter protein "A". The probable initiation site was identified as an ATG codon beginning at position 494. This start condon is preceded by two possible initiation sequences, a TATAAAG sequence beginning at position 104, and a TATAT sequence beginning at position 400. The amino acid sequence of protein A, and its position in the HBV-DNA nucleotide sequence are shown in Table 2 and in FIG. 4.

Gel electrophoresis of a Dane particle preparation in sodium dodecyl sulfate revealed a prominent band of protein having a M.W. of about 80,000, consistent with the hypothesis that the protein band is composed of protein A. It is possible that protein A is the DNA polymerase associated with Dane particles.

A small protein, "protein B", was identified in reading frame 2, as shown in Table 2 and FIG. 4. It is noted that the number of nucleotides in the HBV genome is not evenly divisible by 3. By continuous tracking of the genome, triplet by triplet, one eventually encounters all possible triplets in all possible reading frames, in three circuits of the genome. In the case of protein B, there exists a possible overlap region in which the sequence coding for the C-terminal end of protein B also codes for that part of the "possible N-terminal" core gene region shown in FIG. 4, in a different reading frame.

The major identified coding regions of HBV-DNA were found to be transcribed in the same reading direction, hence from the same strand. The complementary strand sequence was found to have numerous termination codons in all reading frames. Two possible coding regions for small proteins of 90 and 60 amino acids were located, the largest of which is mapped in FIG. 4.

EXAMPLE 11

Antibody Formation in Experimental Animals

The trp E-S protein fusion protein described in Example 5 and the S-protein described in Example 6 are sufficiently antigenic to elicit antibodies. The antibodies are cross-reactive with HBsAg. Guinea pigs are injected subcutaneously at 9, 14, and 56 day intervals with 10 ml physiological saline or phosphate-buffered saline containing 500 μg S-protein or trp E-S protein fusion product, as described in Examples 5 and 6, respectively, purified as described. The serum of the test animals is sampled at 0, 28, 56 and 84 days and assayed for antibody titer against Dane particles of HBsAg partially purified from infectious serum. The radioimmunoassay of Hollingren, F., et al., supra, is employed. The majority of animals exhibit antibodies cross-reactive with HBsAg 84 days after administration of the protein. Similar results are obtained upon injection of monkeys. Accordingly, the immunologically active protein constituents of HBV, expressed by a microorganism that has been transferred by a DNA transfer vector encoding said protein are capable of eliciting antibodies cross-reactive with an immunologically reactive component of the virus.

The described proteins have the advantage of being available in significantly larger quantities than HBsAg obtained from Dane particles or carrier serum. Furthermore, there is no danger of accidental infection since there is no intact virus in the trp E-S protein expression product, nor in the S-protein. By contrast, viral proteins purified from serum always pose the danger of viral contamination.

EXAMPLE 12

As shown in Example 11, protein coded by the genome of an NP virus and synthesized by a microorganism is capable of eliciting antibodies cross-reactive with an immunologically reactive component of said NP virus. Furthermore, derivatives and fusion protein products of such microorganism synthesized proteins are antigenic and capable of eliciting antibodies cross-reactive with an immunologically reactive component of the NP virus. It therefore follows that such proteins and protein derivatives, when purified as described and administered in a physiologically acceptable medium, constitute a vaccine for protection against infection by the virus.

Sixteen chimpanzees are divided into three groups. Group A (6 animals) is inoculated intravenously with 1.0 ml of B.O.B. Hepatitis B virus; Group B (4 animals) is inoculated intravenously with 1.0 ml containing 5 mg. of trpE-S protein fusion protein, synthesized and purified as described in Example 5, in physiological saline; Group C (6 animals) is the control group and receives no inoculation. All chimpanzees in Group A have evidence of clinical hepatitis B (either antigenemia, enzyme elevations and/or antibody response) within forty weeks. None of the animals in Groups B or C show evidence of clinical hepatitis B infection over the same 40-week period. The chimpanzees of Group B are rendered immune to subsequent challenge when inoculated intravenously with 1.0 ml of B.O.B. hepatitis B virus.

The S protein or a derivative thereof as described in Example 6, may be employed in a similar fashion to provide the desired immunological response.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A vector comprising a first DNA sequence which encodes the full-length hepatitis B surface antigen S-protein wherein said vector is free of the nucleotide sequence encoding the hepatitis B core antigen wherein said first DNA sequence is operably linked to a second DNA sequence capable of effecting expression of said first DNA sequence in a microorganism, which second DNA sequence contains a promoter operable in said microorganism.

2. The vector of claim 1 wherein said first DNA encodes an S-protein of the amino acid sequence:

| | | | | | | | | | |
|---|---|---|---|---|---|---|---|---|---|
| MET | GLU | ASN | ILE | THR | SER | GLY | PHE | LEU | GLY |
| PRO | LEU | LEU | VAL | LEU | GLN | ALA | GLY | PHE | PHE |
| LEU | LEU | THR | ARG | ILE | LEU | THR | ILE | PRO | GLN |
| SER | LEU | ASP | SER | TRP | TRP | THR | SER | LEU | ASN |
| PHE | LEU | GLY | GLY | SER | PRO | VAL | CYS | LEU | GLY |
| GLN | ASN | SER | GLN | SER | PRO | THR | SER | ASN | HIS |
| SER | PRO | THR | SER | CYS | PRO | PRO | ILE | CYS | PRO |
| GLY | TYR | ARG | TRP | MET | CYS | LEU | ARG | ARG | PHE |
| ILE | ILE | PHE | LEU | PHE | ILE | LEU | LEU | LEU | CYS |
| LEU | ILE | PHE | LEU | LEU | VAL | LEU | LEU | ASP | TYR |
| GLN | GLY | MET | LEU | PRO | VAL | CYS | PRO | LEU | ILE |
| PRO | GLY | SER | THR | THR | THR | SER | THR | GLY | PRO |
| CYS | LYS | THR | CYS | THR | THR | PRO | ALA | GLN | GLY |
| ASN | SER | MET | PHE | PRO | SER | CYS | CYS | CYS | THR |
| LYS | PRO | THR | ASP | GLY | ASN | CYS | THR | CYS | ILE |
| PRO | ILE | PRO | SER | SER | TRP | ALA | PHE | ALA | LYS |
| TYR | LEU | TRP | GLU | TRP | ALA | SER | VAL | ARG | PHE |
| SER | TRP | LEU | SER | LEU | LEU | VAL | PRO | PHE | VAL |
| GLN | TRP | PHE | VAL | GLY | LEU | SER | PRO | THR | VAL |
| TRP | LEU | SER | ALA | ILE | TRP | MET | MET | TRP | TYR |
| TRP | GLY | PRO | SER | LEU | TYR | SER | ILE | VAL | SER |
| PRO | PHE | ILE | PRO | LEU | LEU | PRO | ILE | PHE | PHE |
| CYS | LEU | TRP | VAL | TYR | ILE. | | | | |

3. The vector of claim 1 wherein the first DNA sequence encodes a protein of the formula X-S-Y, wherein S represents the S-protein of hepatitis B virus, Y is OH or $NH_2$ and X is selected from the group consisting of H, pre-S2, pre-S1/pre-S2, and a peptide encoded by pre-S1/pre-S2 and containing at least the 9 amino acid sequence at the C-terminus of pre-S2.

4. The vector of claim 3 wherein the pre-S1/pre-S2 has the amino acid sequence:

| | | | | | | | | | | | | | | |
|---|---|---|---|---|---|---|---|---|---|---|---|---|---|---|
| MET | GLY | TRP | SER | LYS | PRO | ARG | LYS | GLY | MET | GLY | THR | ASN | LEU | SER |
| VAL | PRO | ASN | PRO | LEU | GLY | PHE | PRO | ASP | HIS | GLN | LEU | ASP | PRO | ALA |
| PHE | GLY | ALA | ASN | SER | ASN | PRO | ASP | TRP | ASP | PHE | ASN | PRO | VAL | LYS |
| ASP | TRP | PRO | ALA | ASN | GLN | VAL | GLY | VAL | GLY | ALA | PHE | GLY | PRO | ARG |
| LEU | THR | PRO | HIS | GLY | ILE | LEU | GLY | TRP | SER | PRO | GLN | ALA | GLN | GLY |
| ILE | LEU | THR | VAL | SER | THR | ILE | PRO | ALA | SER | THR | ASN | ARG | GLN | SER |
| GLY | ARG | GLN | PRO | THR | PRO | ILE | SER | PRO | LEU | ARG | ASP | SER | HIS | PRO |
| GLN | ALA | MET | GLN | TRP | ASN | SER | THR | ALA | PHE | HIS | GLN | THR | LEU | GLN |

-continued

| | | | | | | | | | | | | | | |
|---|---|---|---|---|---|---|---|---|---|---|---|---|---|---|
| ASP | PRO | ARG | VAL | ARG | GLY | LEU | TYR | LEU | PRO | ALA | GLY | SER | GLY | THR |
| VAL | ASN | PRO | ALA | PRO | ASN | ILE | ALA | SER | HIS | ILE | SER | ILE | SER | ALA |
| ARG | THR | GLY | ASP | PRO | VAL | THR | ASN. | | | | | | | |

5. The vector of claim 3 wherein the pre-S2 has the amino acid sequence:

| | | | | | | | | | | | | | | |
|---|---|---|---|---|---|---|---|---|---|---|---|---|---|---|
| MET | GLN | TRP | ASN | SER | THR | ALA | PHE | HIS | GLN | THR | LEU | GLN | ASP | PRO |
| ARG | VAL | ARG | GLY | LEU | TYR | LEU | PRO | ALA | GLY | SER | GLY | THR | VAL | ASN |
| PRO | ALA | PRO | ASN | ILE | ALA | SER | HIS | ILE | SER | ILE | SER | ALA | ARG | THR |
| GLY | ASP | PRO | VAL | THR | ASN. | | | | | | | | | |

6. The vector of claim 1 wherein said second DNA sequence comprises the *E. coli* trp promoter.

7. A microorganism capable of producing a protein immunoreactive with antibodies raised against hepatitis B surface antigen which has been transfected with the vector of claim 1.

8. A microorganism capable of producing a protein immunoreactive with antibodies raised against hepatitis B surface antigen which has been transfected with the vector of claim 2.

9. A microorganism capable of producing a protein immunoreactive with antibodies raised against hepatitis B surface antigen which has been transfected with the vector of claim 3.

10. A method to produce a protein immunoreactive with antibodies raised against hepatitis B surface antigen which comprises culturing the microorganism of claim 7 under conditions under which said first DNA sequence is expressed to produce protein immunoreactive with antibodies raised against hepatitis B surface antigen, and recovering the protein immunoreactive with antibodies raised against hepatitis B surface antigen.

11. A method to produce a protein immunoreactive with antibodies raised against hepatitis B surface antigen which comprises culturing the microorganism of claim 8 under conditions under which said first DNA sequence is expressed to produce protein immunoreactive with antibodies raised against hepatitis B surface antigen, and recovering the protein immunoreactive with antibodies raised against hepatitis B surface antigen.

12. A method to produce a protein immunoreactive with antibodies raised against hepatitis B surface antigen which comprises culturing the microorganism of claim 9 under conditions under which the trp promoter is repressed, derepressing the trp promoter to permit expression of the first DNA, and recovering the protein immunoreactive with antibodies raised against hepatitis B surface antigen.

* * * * *